United States Patent [19]

Cosentino et al.

[11] Patent Number: 5,400,818

[45] Date of Patent: Mar. 28, 1995

[54] SENSOR FOR PERACETIC ACID-HYDROGEN PEROXIDE SOLUTION

[75] Inventors: Louis C. Cosentino, Deephaven; David C. Gust, Andover; Roger L. Funk, Cedar; Gerald J. Rinehart, Isanti; Vernon S. Taaffe, New Hope, all of Minn.

[73] Assignee: Minntech Corporation, Minneapolis, Minn.

[21] Appl. No.: 157,143

[22] PCT Filed: Jun. 18, 1991

[86] PCT No.: PCT/US91/04295

§ 371 Date: Dec. 8, 1993

§ 102(e) Date: Dec. 8, 1993

[87] PCT Pub. No.: WO92/22808

PCT Pub. Date: Dec. 23, 1992

[51] Int. Cl.[6] ............................................. G01N 27/07
[52] U.S. Cl. ................................. 137/551; 137/93; 137/607; 324/439; 324/691; 340/603; 422/82.03
[58] Field of Search ............... 137/551, 240, 5, 93, 137/605, 607; 324/439, 691; 340/603; 422/82.02, 82.03

[56] References Cited

U.S. PATENT DOCUMENTS

| | | | |
|---|---|---|---|
| 2,439,354 | 4/1948 | Wolcott | 340/603 |
| 3,013,572 | 12/1961 | Lahti et al. | 137/5 X |
| 3,263,224 | 7/1966 | Berman et al. | 340/603 |
| 3,918,469 | 11/1975 | Zamboni et al. | 137/5 |
| 4,142,539 | 3/1979 | Shih et al. | 134/113 |
| 4,536,274 | 8/1985 | Papadakis et al. | 204/433 |
| 4,668,944 | 5/1987 | Teass | 340/603 |
| 4,803,466 | 7/1989 | Gurstein et al. | 340/603 |
| 4,963,815 | 10/1990 | Hafeman | 324/715 |

Primary Examiner—Stephen M. Hepperle
Attorney, Agent, or Firm—Barbara A. Wrigley

[57] ABSTRACT

Concentrations of stock hydrogen peroxide-peracetic acid solutions can be monitored resistively. The resistivity cell electrodes have titanium surfaces which resist corrosion better than other electrode materials including platinum electrodes. Such resistivity monitoring is particularly useful to verify the concentrations of sterilant stock solutions used in machinery for cleaning and sterilizing medical and dental equipment such as dialyzer reuse machines. Over the temperature range of interest the resistivity measurement is substantially not affected by changes of temperature in the room temperature range.

7 Claims, 3 Drawing Sheets

SENSOR FOR PERACETIC ACID-HYDROGEN PEROXIDE SOLUTION

BACKGROUND OF THE INVENTION

It has generally become accepted that expensive apparatus particularly that used in medical and dental applications need be recycled by cleaning and sterilizing before reuse. Much of the apparatus for such purposes requires very special handling in order to insure that it is in fact sterile. It is often not practicable to use thermal means to accomplish such sterilizing and therefore various chemical sterilizing agents have found use. It is of extreme importance that a high degree of confidence exist in the products that are going to be utilized for the sterilizing to insure that they have been properly mixed prior to being actually used for the sterilization purpose. One normally starts with a concentrate of the active materials to be used and dilutes them down with water to the desired level for actual sterilization. It is important that the active material be neither over nor under diluted.

Sterilants of the peracetic acid-hydrogen peroxide types have been known for many years. The sterilants are prepared by mixing acetic acid and hydrogen peroxide to give an equilibrated solution of peracetic acid, acetic acid and hydrogen peroxide. When properly mixed and diluted, these solutions have shown great efficacy in killing not only bacteria but various other microbiological materials. A great deal of literature and patent material exist in dealing broadly with peracetic acid-hydrogen peroxide solutions for sterilization. Without limitation, the reader is directed to U.S. Pat. Nos. Bowing 4,051,058 and 4,051,059. The reader's attention is also directed to the text ORGANIC PEROXIDES by Daniel Swern and to M. G. C. Boldry, "The Bactericidal, Fungicidal and Sporicidal Properties of Hydrogen Peroxide and Peracetic Acid," *J. App. Bacteriology* 54, 417–423 for further background on the field of the use of peroxides and hydrogen peroxide in microbiological applications.

In U.S. Pat. No. 4,517,081 there is described a machine which cleans and sterilizes dialyzers to enable their reuse. The machine includes means for passing the series of cleaning, sterilizing and rinsing fluids through the compartments of the dialyzer in a predetermined sequence. Predetermined dilutions of stock solutions are accomplished in a fluid tank within the machine which communicates with a microprocessor controlled manifold for introducing controlled amounts of stock solutions and water into the tank. Commercial embodiments of the invention have utilized peracetic acid-hydrogen peroxide solutions of different concentrations for both the cleaning and sterilizing functions.

Peracetic-hydrogen peroxide solutions are inherently unstable and, therefore, subject to variation in concentration of active peroxy components with aging. Highly concentrated solutions are more stable. The high concentration of conventional commercial peracetic acid-hydrogen peroxide solutions must be manually diluted before the solution can be conveniently handled as a stock solution in a machine such as described in U.S. Pat. No. 4,517,081. The pre-dilution introduces possibilities for human error in the dilution and, therefore, in the ultimate concentration and uniformity within the diluted concentrate of peracetic acid and hydrogen peroxide used to clean and sterilize the dialyzer. Should the diluted material be too dilute a serious risk of residual living bacteria remains. Too concentrated may result in insufficient rinsing to remove the sterilant and may even damage the material being sterilized.

Conductivity measurements have been widely used to measure concentrations of solutes in solvents and for measuring other parameters indicated by fluid concentration changes. For instance, blood conductivity measurements have been used to monitor cardiac output as described in U.S. Pat. Nos. 3,985,123, 4,572,206, 4,380,237, and Bourdillon et al, Med. & Biol. Eng. & Comput. 17, 323–329 (1979).

While conductivity measurements to monitor concentrations of solutes in aqueous solutions are well known. It is believed that, heretofore, no such measurements have been used to monitor peroxide/peracid solutions concentrations.

SUMMARY OF THE INVENTION

Because of the possibilities of error in the dilution of stock solutions of peracid-peroxide there exists a need to monitor the stock solution to assure that it is neither so strong that the final solution risks damage to the dialyzer or to the cleaning machine, and that it is not so weak that it causes the final solutions to fail in their cleaning and sterilizing functions. The present invention accomplishes these purposes and provides a special electrode and electronic system for insuring that proper mixing has taken place of a concentrate and purified water prior to its actual usage in the overall cleaning and sterilizing system.

This invention relates to a overall system for the monitoring of blending of concentrates and water as a preliminary to actual sterilization of various attendant equipment. More particularly, it is used in conjunction with special electrodes found uniquely suitable for hydrogen peroxide containing solutions and for sterilants of the peracetic acid - hydrogen peroxide type.

As one aspect of the invention, therefore, there is disclosed a machine which automatically dilutes stock solutions of peracetic acid and hydrogen peroxide in a dilution tank for subsequent use as cleaning and sterilizing agents, the improvement comprising that the machine is provided with a concentration sensing and warning means for determining the value of concentration dependent parameters of the stock solution and warning if that value is outside a predetermined range.

In a further aspect of the invention there is provided a sensor for measuring the resistivity of a peracetic acid-hydrogen peroxide solution comprising a spaced pair of titanium electrodes, resistivity measuring means communicating with said electrodes when said electrodes are in contact with the solution, said measuring means providing an output indicative of the resistivity of the solution, comparison means for comparing said resistivity indicative output with a predetermined range of acceptable outputs and issuing a warning signal when said conductivity indicative output is outside said range of acceptable outputs.

DESCRIPTION OF THE PREFERRED EMBODIMENTS

Figure 1:
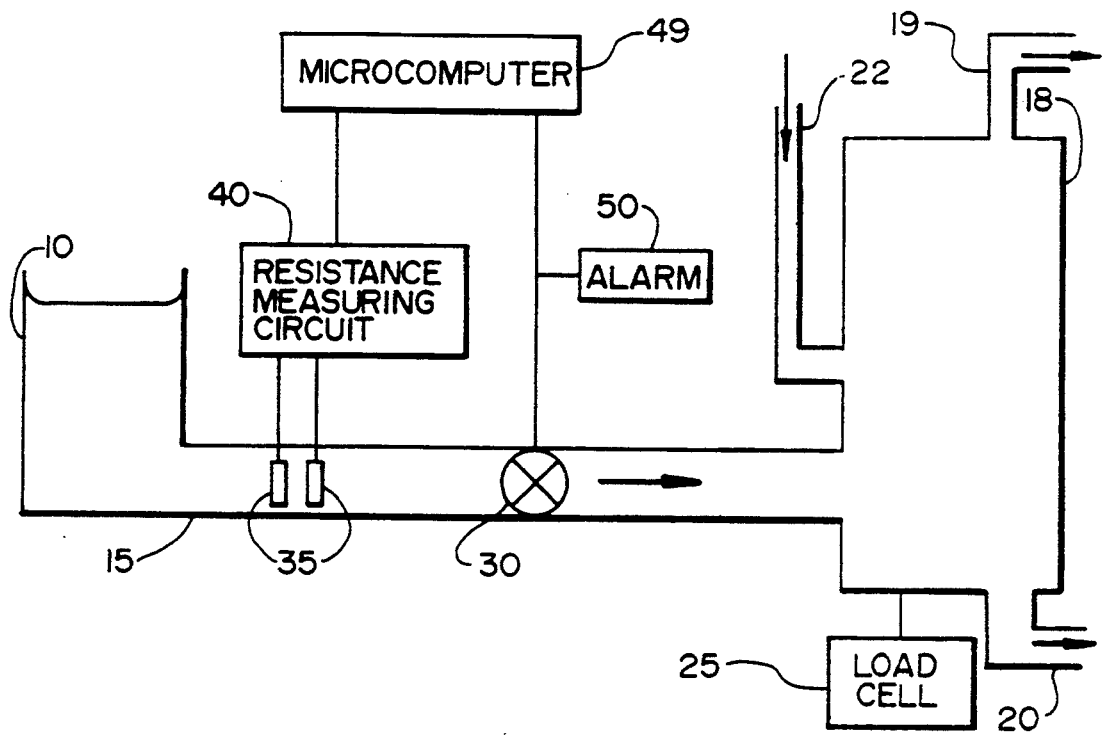
FIG. 1 is a schematic representation of a portion of a dialyzer cleaning and sterilizing machine incorporating the sensor of the invention.

Referring to FIG. 1, there is depicted schematically a portion of the preferred embodiment of the invention wherein the resistivity sensor of the invention is employed in a machine which automatically dilutes stock solutions cleaning and sterilizing fluid and circulates them for cleaning an article such as a dialyzer or other medical or dental apparatus. Fluid flow directions in FIG. 1 are indicated by the arrows.

A stock solution of hydrogen peroxide-peracetic acid is held in a container 10 which communicates with a dilution tank 18 by means of a conduit 15. A valve 30 and conduit 15 operate to control the flow of the stock solution into the dilution tank 18.

The valve is controlled by a microprocessor which opens and closes the valve in accordance with a predetermined program for controlling the circulation of fluids through the machine. Spaced probes 35 in conduit 15 upstream of the valve 30 form a resistivity cell for sensing the resistivity of the fluid passing thereby. Probes 35 are electrically connected to a resistivity measuring circuit 40 which issues an output to the microprocessor as described in detail below.

The tank 18 is also provided with a connection to a vacuum source 19, a fluid outlet 20 communicating with the article or articles to be cleaned and a water inlet 22. Valves not shown in each of the respective inlets and outlets are also suitably provided and controlled by the microcomputer. The tank sits on a load cell 25 whose output is also fed into the microcomputer. The load cell 25 allows monitoring of the volume of the fluids in dilution tank 18 so that preprogrammed dilutions and fluid circulations may be performed by the microcomputer. For further details on the construction and operation of such a machine, the reader is referred to U.S. Pat. No. 4,517,081.

Figure 2:
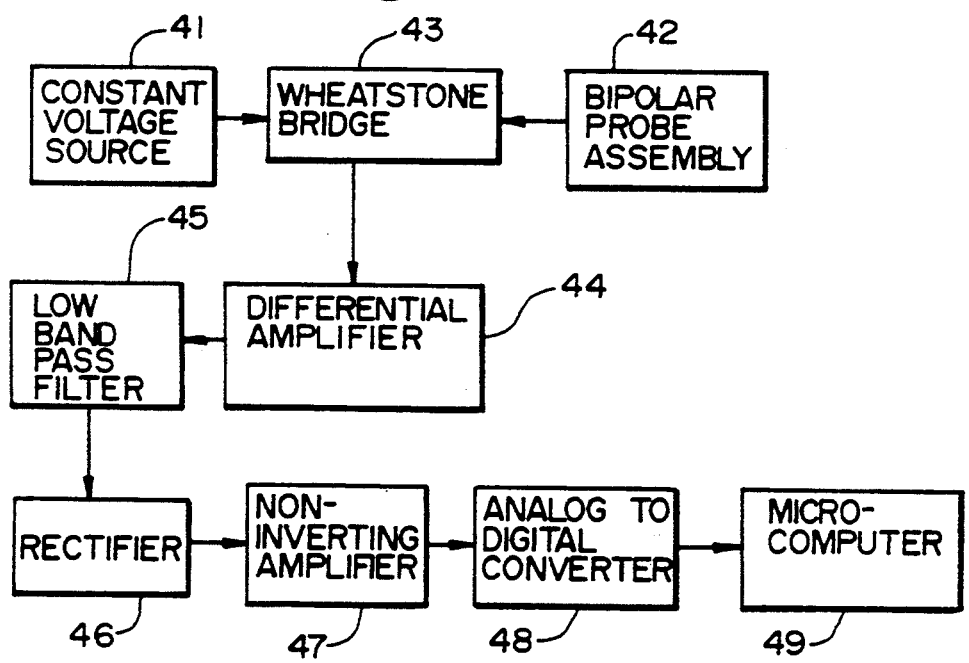
FIG. 2 is a schematic representation of the preferred embodiment of the resistivity measuring circuit.

The resistivity measuring circuit preferably utilizes a constant voltage source. FIG. 2 depicts the elements of the preferred circuit. A constant voltage source 41, from a 1KHz sine wave oscillator applies a voltage across the bipolar electrode probe assembly 42 through a Wheatstone bridge 43. Suitably the bipolar probe assembly 42 comprises the two electrodes 35 of FIG. 2. The output of the Wheatstone bridge is fed to a differential amplifier 44 which is provided with a gain of 10 and which converts the sensed current in the bridge circuit to a voltage proportional to the resistance across the probe assembly. The amplified signal is conditioned by feeding through a band pass filter 45, desirably a 2-pole filter having a center frequency of 1000 Hz and 3db points of 500 and 1500 Hz. The conditioned signal is then sent to a rectifier 46. Suitably, the rectifier 46 is a full wave rectifier circuit having a voltage gain of two and having its gain temperature compensated. The rectified signal is then fed to a non-inverting amplifier 47 which has a gain of 2 and has a capability of offset adjustment. Next the signal passes through an analog-to-digital converter 48 to provide an eight-bit digital converted signal. The converted signal is ultimately fed to a microcomputer 9 where it is compared to a preprogrammed range of acceptable signal values for the stock solution. If the measured signal is within the preprogrammed range the machine will continue to operate normally. If outside the acceptable range, a machine error is indicated and an alarm signal is issued. Suitably the alarm signal triggers an audible or visual alarm 50 and also triggers an automatic shutoff of the valve 30 to stop flow of the stock solution into the cleaning machine.

In attempting to develop a resistivity sensor for the peroxide/peracid system it was discovered that electrode metals such as stainless steel and other metals and, in deed, even conventional platinum or platinum-black electrodes were rapidly corroded by the solution and, therefore, unsuitable. Signs of corrosion appeared in a matter of minutes. However, it has unexpectedly been discovered that titanium metal electrodes are sufficiently inert to allow their use in relatively concentrated peroxide/peracid solutions. Titanium electrodes showed no signs of corrosion after weeks of immersion.

The electrodes are preferably titanium having a configuration of round with hemispherically shaped ends. The electrodes may conveniently be 0.25" in diameter, and spaced from center to center by about 1.0".

The resistance of the subject solutions is relatively constant over a fairly wide range of temperatures including normal ambient temperatures of about 18°–25° C. Consequently, little or no correction need to be made for normal temperature variations.

It is recommended that a calibration test be seen for the specific peracetic acid hydrogen peroxide mixture to be used to establish the curves for concentration limits that will be used to set the alarm levels in the microcomputer.

In operation a commercial peracetic acid-hydrogen peroxide concentrate (which may be, for example, Renalin ® available from Minntech Corporation of Minneapolis, Minn. is prediluted to a stock solution in the container 10. Renalin ® has a nominal composition in the concentrate of about 23% of $H_2O_2$, 5% peracetic acid and 9% acetic acid balance $H_2O$. The dilution tank 18 is tared with load cell 25. Valve 30 is then opened to allow the stock solution to be drawn into the dilution tank by means of the vacuum source 19. As the stock solution flows past the electrodes 35 the resistance of the solution is checked by the computer to verify that it is within the preprogrammed range of acceptable values. If within the acceptable range, the stock solution is permitted to continue flowing into the dilution tank until a predetermined amount has been drawn in as indicated by the load cell, at which point the valve 30 is closed. Water is added to tank 18 by means of water inlet 22 to dilute the stock solution to a hydrogen peroxide concentration of 1.7% or 3% depending on whether the solution is to be used respectively for initial cleaning or bactericidal sterilizing operations.

If substantial deviations are encountered in the output of the resistivity beyond those calibrated as acceptable the measuring circuit triggers the microcomputer to interrupt the dilution sequence early, closing valve 30 and triggering alarm 50 to alert the operator of the error condition. The stock solution can the be replaced, the dilution tank flushed and the dilution operation restarted.

The invention may be illustrated by the following non-limiting examples.

EXAMPLES

In the following examples stock solutions suitable for use in cleaning and sterilizing a dialyzer reuse machine as described above were prepared by diluting the concentrates such as Renalin ® in the examples to 21% of their concentrate strength with highly purified water (2 liters concentrate made up to 9.46 liters (2.5 gal.)). Resistance measurements were made on the stock solutions.

EXAMPLE I

Figure 3:
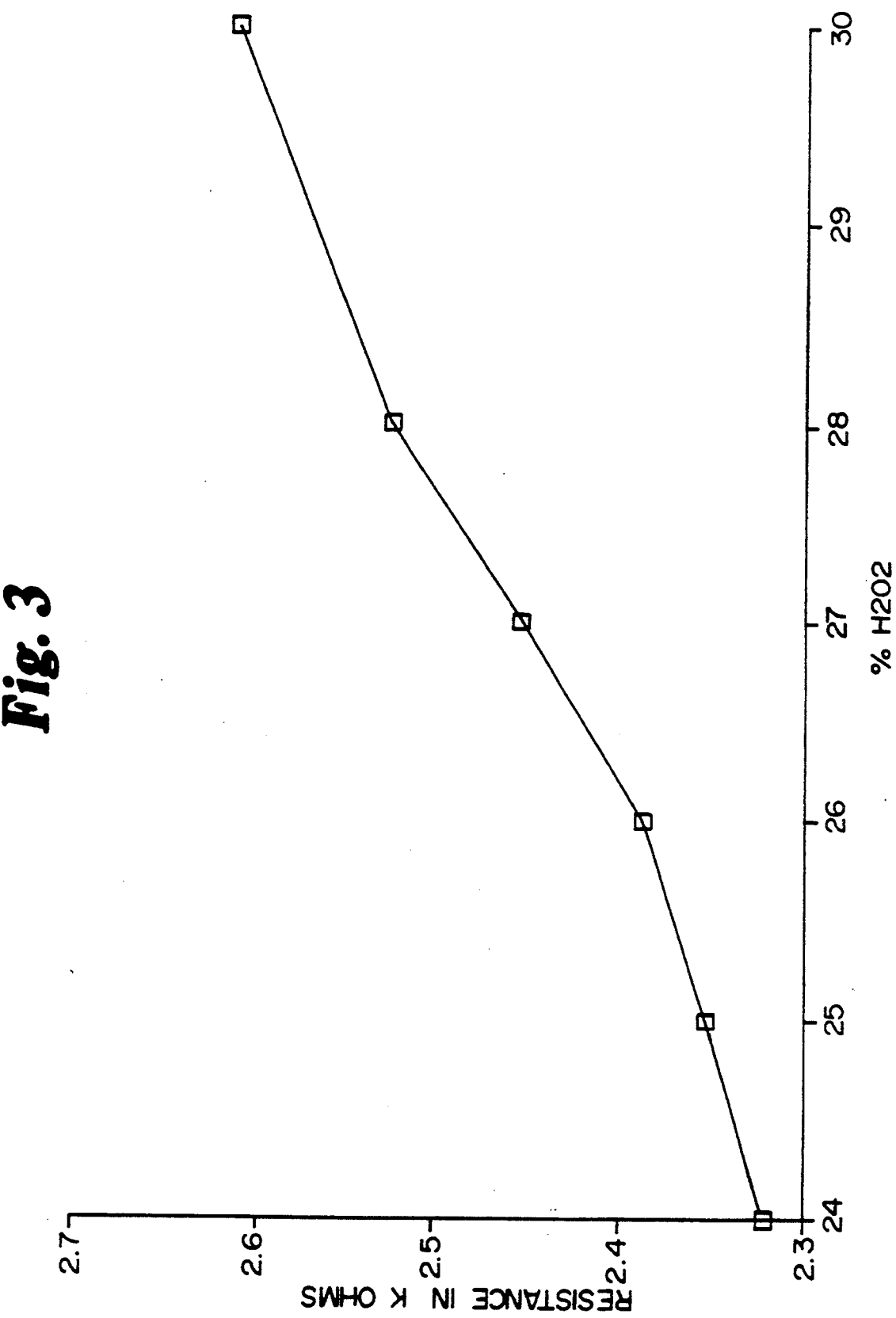
FIG. 3 is a graph showing the resistance of a solution without stabilizer useful in the present invention as a function of the percentage of hydrogen peroxide in the solution.

Stock solutions were prepared from the concentrates as referred to above and resistances measured with a sensor of the invention. FIG. 3 is a plot of the measured resistance as a function of the initial peroxide concentration. The substantially linear relationship demonstrates that a mixture of peracetic and peroxide concentration can be successfully monitored resistivity in this complex solution.

EXAMPLE II

Temperature and Aging Dependence

Hydrogen peroxide-peracetic acid stock solutions were used in this experiment. The stock solutions were prepared for the following ingredients:

Renalin ® diluted to 21% of concentrate to a stock solution. These were tested as freshly made and after standing for several days and are labeled E fresh and E aged.

Other formulations having compositions of the following were made and tested:

A. 30% $H_2O_2$, 12.85% HOAc to give peracetic acid concentration of about 5%.

B. 27% $H_2O_2$; 12.85% HOAc to give peracetic acid concentration of about 5%.

C. 24%, $H_2O_2$; 12.85% HOAc to give a peracetic acid concentration of about 4%.

Figure 4:
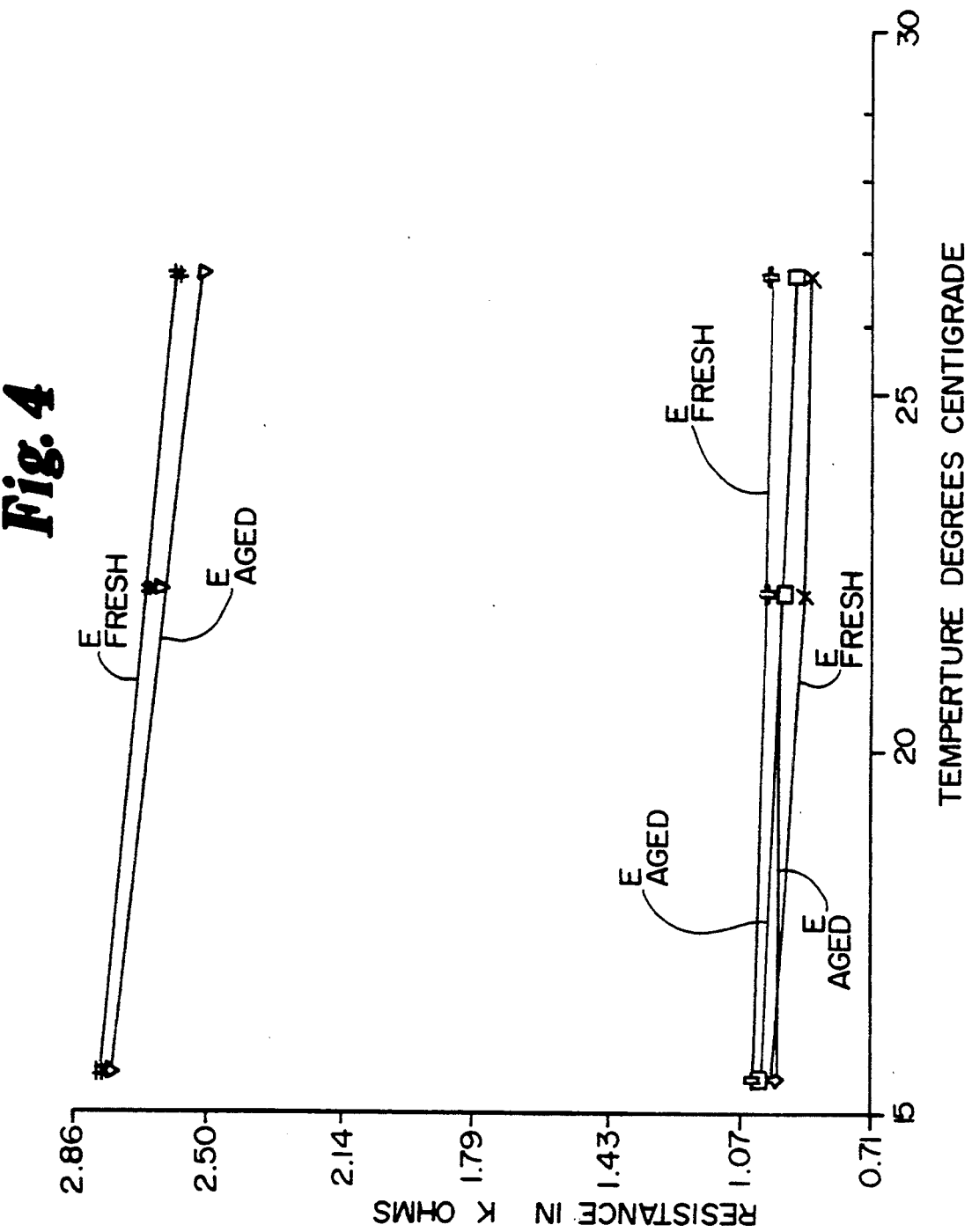
FIG. 4 is a plot of the change in resistivity of six different solutions of 21% dilution as a function of temperature.

The resistances of stock solutions prepared as described above were measured and plotted as a function of temperature on both fresh and aged stock solution using a resistivity cell having titanium electrodes as described previously. As can be seen in FIG. 4, the plot of the resistivity as measured was substantially flat showing the virtual lack of temperature dependence over a room temperature range of about 15° C. to 26.6° C. The upper curves are for Renalin ® concentrate as a starting point and the lower curves are for formulations of A, B and C.

While the invention has been described above with regard to the preferred embodiment, it will be readily apparent that the invention is not so limited. For instance the sensor may just as usefully be employed in a machine for cleaning and sterilizing dental or surgical equipment or the like. These and other modifications within the skill of those in the art should be considered within the scope of the invention which is limited only by the language of the following claims and their legal equivalents.

What is claimed is:

1. In a machine which automatically dilutes stock solutions of peracetic acid and hydrogen peroxide for subsequent use as cleaning and sterilizing agents, the improvement comprising:

a concentration and sensing means operably in contact with the stock solution prior to use of the stock solution as cleaning and sterilizing agents for determining a resistively measured value of a composition peroxide concentrate dependent parameter of the stock solution and issuing an alarm signal if that value is outside a predetermined acceptable range.

2. A machine as in claim 1 wherein said concentration and sensing means includes a resistivity measuring cell in contact with the stock solution and having a pair of titanium electrodes spaced apart from one another by less than 3 centimeters.

3. A machine as in claim 1 wherein said concentration and sensing means comprises:

a resistivity measuring cell in contact with the stock solution and having a pair of electrodes;

resistivity measuring means for communicating with said electrodes and providing as an output said value indicative of the resistivity of the solution; and comparison means for comparing said resistivity indicative output with said predetermined acceptable range and issuing said alarm signal when said resistivity indicative output is outside the acceptable range.

4. A machine as in claim 3 wherein said resistivity measuring means comprises a constant voltage source which applies a constant voltage to said electrodes through a bridge circuit, the bridge circuit providing a signal which is fed sequentially through a differential amplifier, a band pass filter, a rectifier, a non-inverting amplifier and an analog to digital converter to yield a digital signal indicative of the resistivity of said solution.

5. A machine as in claim 4 wherein said digital signal is said resistivity indicative output, and said comparison means comprises a microcomputer preprogrammed with said predetermined range of acceptable output signals.

6. A machine as in claim 1 further comprising shut down means responsive to said alarm signal for interrupting operation of the machine when said alarm signal is issued.

7. A machine as in claim 6 having a stock solution tank for holding said stock solution prior to dilution, a dilution tank wherein said dilution is performed and a conduit between said tanks, the shut down means comprising a valve in said conduit which is controlled to close in response to said alarm signal.

* * * * *

UNITED STATES PATENT AND TRADEMARK OFFICE
CERTIFICATE OF CORRECTION

PATENT NO. : 5,400,818
DATED : March 28, 1995
INVENTOR(S) : Cosentino, et al.

It is certified that error appears in the above-indentified patent and that said Letters Patent is hereby corrected as shown below:

Column 4, line 64, delete "the" (1st occurrence) substitute —then—

Column 5, line 46, delete "C." substitute --C-- therefor

Signed and Sealed this

Twenty-ninth Day of August, 1995

Attest:

BRUCE LEHMAN

Attesting Officer

Commissioner of Patents and Trademarks